United States Patent [19]
Danes

[11] Patent Number: 6,108,823
[45] Date of Patent: Aug. 29, 2000

[54] INTERCONNECTED UNDERGARMENT AND DIAPER COMBINATION

[76] Inventor: John Danes, R.R. #2 Box 168, Kingsland, Tex. 78639-9629

[21] Appl. No.: 09/190,575

[22] Filed: Nov. 12, 1998

[51] Int. Cl.⁷ .................................................. A41D 13/04
[52] U.S. Cl. .................................................. 2/403; 2/400
[58] Field of Search ............................ 2/400–408, 227, 2/228, 238; 604/385.1, 386, 393, 387, 389–391, 394, 397–399

[56] References Cited

U.S. PATENT DOCUMENTS

| | | | |
|---|---|---|---|
| 1,329,119 | 1/1920 | George | 2/400 |
| 1,928,330 | 9/1933 | DeDeWitt | 2/400 |
| 2,034,312 | 3/1936 | Rubin | 2/400 |
| 2,292,030 | 8/1942 | Kraft | 2/400 |
| 2,544,620 | 3/1951 | Steinart | 2/400 |
| 2,599,769 | 6/1952 | MacRae et al. | 2/400 |
| 3,039,466 | 6/1962 | Wilson | 2/400 |
| 4,615,695 | 10/1986 | Cooper | 2/400 |
| 5,386,595 | 2/1995 | Kuen et al. | 2/400 |

Primary Examiner—Gloria M. Hale

[57] ABSTRACT

An incontinence system is provided including a reusable undergarment with a first couple attached thereto. Associated therewith is a disposable incontinence diaper with a second couple attached thereto. The incontinence diaper may be removably positioned within the undergarment and the couples may be releasably coupled to maintain fixed relative positioning of the diaper and undergarment.

6 Claims, 2 Drawing Sheets

INTERCONNECTED UNDERGARMENT AND DIAPER COMBINATION

BACKGROUND OF THE INVENTION

1. Field of the Invention

The present invention relates to diapers and more particularly pertains to a new interconnected undergarment and diaper combination for allowing the effective combined use of a reusable undergarment and a disposable diaper.

2. Description of the Prior Art

The use of diapers is known in the prior art. More specifically, diapers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,578,072; 2,273,542; U.S. Patent Des. 345,015; U.S. Patent Nos. 3,406,688; 4,505,706; and 5,304,161.

In these respects, the interconnected undergarment and diaper combination according to the present invention substantially departs from the conventional concepts and designs of the prior art, and in so doing provides an apparatus primarily developed for the purpose of allowing the effective combined use of a reusable undergarment and a disposable diaper.

SUMMARY OF THE INVENTION

In view of the foregoing disadvantages inherent in the known types of diapers now present in the prior art, the present invention provides a new interconnected undergarment and diaper combination construction wherein the same can be utilized for allowing the effective combined use of a reusable undergarment and a disposable diaper.

The general purpose of the present invention, which will be described subsequently in greater detail, is to provide a new interconnected undergarment and diaper combination apparatus and method which has many of the advantages of the diapers mentioned heretofore and many novel features that result in a new interconnected undergarment and diaper combination which is not anticipated, rendered obvious, suggested, or even implied by any of the prior art diapers, either alone or in any combination thereof.

To attain this, the present invention generally comprises a reusable undergarment constructed from a cloth linen material. Such undergarment includes a front portion, a rear portion, and a bottom portion integrally coupled. As such, a top circular waist opening is defined with a peripheral edge residing in a common plane. Further defined is a pair of bottom circular leg openings each with a peripheral edge. As shown in the Figures, the undergarment includes an elastic waist strap mounted along the peripheral edge of the waist opening. Further, a pair of elastic leg straps are mounted along the peripheral edges of the leg openings. As shown in FIG. 1, the elastic waist strap has an inner surface with a first pair of spaced buttons mounted thereon adjacent to ends of the front portion and a second pair of spaced buttons mounted thereon adjacent to ends of the rear portion. As such, the first pair of buttons and the second pair of buttons are axially aligned. Next provided is a disposable incontinence diaper constructed from an absorbent material. Similar to the undergarment, the diaper includes the portions, openings and straps. As an option, the diaper may be of a slightly smaller size with respect to the undergarment. As shown in FIG. 1, the elastic waist strap of the diaper has an inner surface with a first pair of spaced horizontal slots formed therein adjacent to ends of the front portion. Further, a second pair of spaced horizontal slots are formed in such waist strap adjacent to ends of the rear portion. As such, the first pair of slits and the second pair of slits are aligned. In use, the incontinence diaper is removably positioned within the undergarment. Further, the buttons of the undergarment are removably inserted within corresponding slits of the incontinence diaper for maintaining fixed relative positioning.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new interconnected undergarment and diaper combination apparatus and method which has many of the advantages of the diapers mentioned heretofore and many novel features that result in a new interconnected undergarment and diaper combination which is not anticipated, rendered obvious, suggested, or even implied by any of the prior art diapers, either alone or in any combination thereof.

It is another object of the present invention to provide a new interconnected undergarment and diaper combination which may be easily and efficiently manufactured and marketed.

It is a further object of the present invention to provide a new interconnected undergarment and diaper combination which is of a durable and reliable construction.

An even further object of the present invention is to provide a new interconnected undergarment and diaper combination which is susceptible of a low cost of manufacture with regard to both materials and labor, and which accordingly is then susceptible of low prices of sale to the consuming public, thereby making such interconnected undergarment and diaper combination economically available to the buying public.

Still yet another object of the present invention is to provide a new interconnected undergarment and diaper combination which provides in the apparatuses and methods of the prior art some of the advantages thereof, while simultaneously overcoming some of the disadvantages normally associated therewith.

Still another object of the present invention is to provide a new interconnected undergarment and diaper combination for allowing the effective combined use of a reusable undergarment and a disposable diaper.

Even still another object of the present invention is to provide a new interconnected undergarment and diaper combination that includes a reusable undergarment with a first couple attached thereto. Associated therewith is a disposable incontinence diaper with a second couple attached thereto. The incontinence diaper may be removably positioned within the undergarment and the couples may be releasably coupled to maintain fixed relative positioning of the diaper and undergarment.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
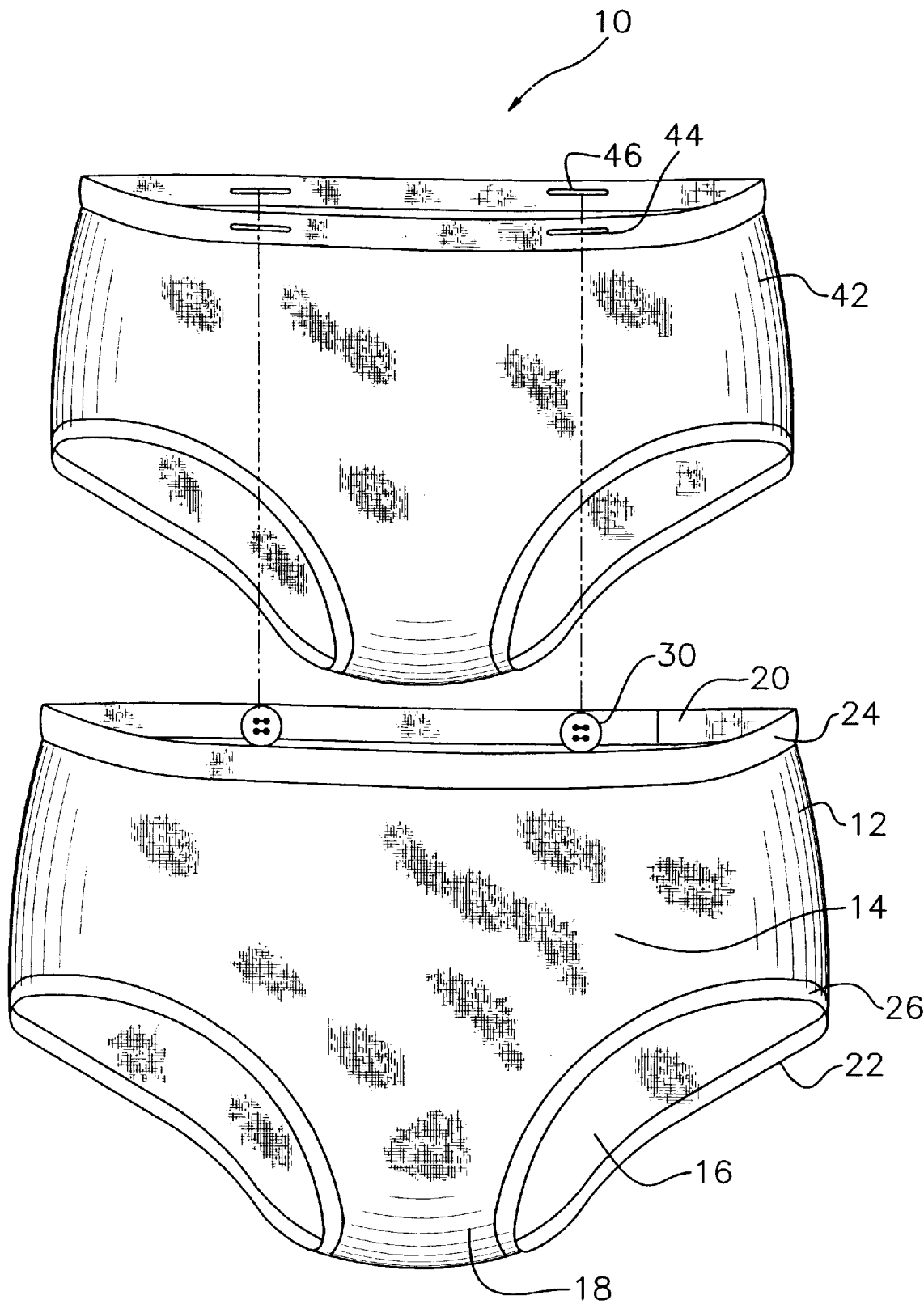
FIG. 1 is an exploded perspective view of a new interconnected undergarment and diaper combination according to the present invention.
Figure 2:
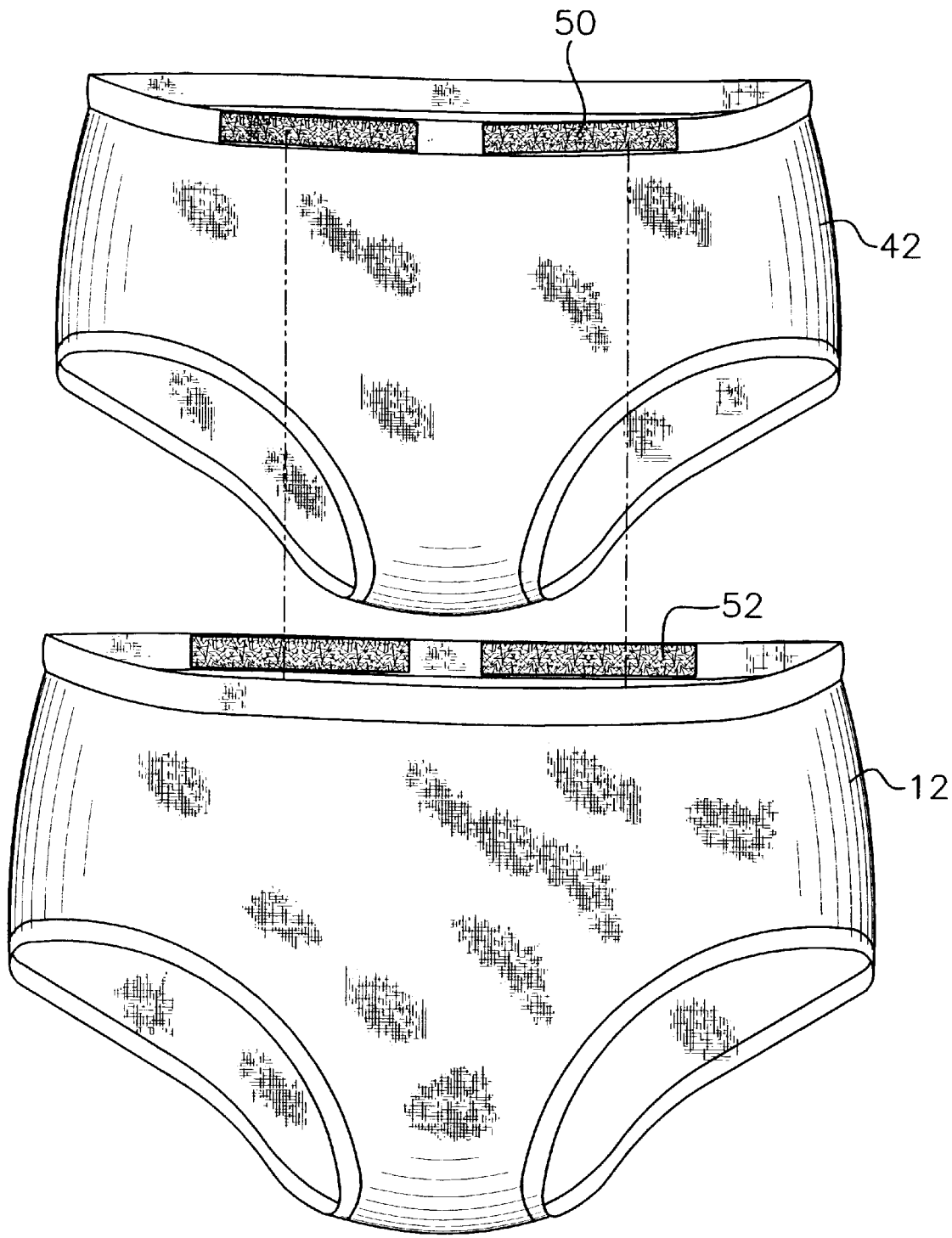
FIG. 2 is an exploded perspective view of another embodiment of the present invention.

With reference now to the drawings, and in particular to FIGS. 1 through 2 thereof, a new interconnected undergarment and diaper combination embodying the principles and concepts of the present invention and generally designated by the reference numeral 10 will be described.

The present invention, designated as numeral 10, includes a reusable undergarment 12 constructed from a cloth or linen material such as cotton, silk, polyester or the like. Such undergarment includes a front portion 14, a rear portion 16, and a bottom portion 18 integrally coupled. As such, a top circular waist opening 20 is defined with a peripheral edge residing in a common plane. Further defined is a pair of bottom circular leg openings 22 each with a peripheral edge.

As shown in the Figures, the undergarment includes an elastic waist strap 24 mounted along the peripheral edge of the waist opening. Further, a pair of elastic leg straps 26 are mounted along the peripheral edges of the leg openings. As shown in FIG. 1, the elastic waist strap has an inner surface with a first pair of spaced buttons mounted thereon adjacent to ends of the front portion and a second pair of spaced buttons 30 mounted thereon adjacent to ends of the rear portion. As such, the first pair of buttons and the second pair of buttons are axially aligned and face each other. Ideally, a center of each button is in approximate alignment with an axis of the associated leg opening of the undergarment. Note FIG. 1.

Next provided is a disposable incontinence diaper 42 constructed from an absorbent material. Similar to the undergarment, the diaper includes the portions, openings and straps. As an option, the diaper may be of a slightly smaller size with respect to the undergarment.

As shown in FIG. 1, the elastic waist strap of the diaper has an inner surface with a first pair of spaced horizontal slots 44 formed therein adjacent to ends of the front portion. Further, a second pair of spaced horizontal slots 46 are formed in such waist strap adjacent to ends of the rear portion. As such, the first pair of slits and the second pair of slits are aligned.

In an alternate embodiment, the outer surface of the waist band of the diaper has a pair of laterally spaced pile fasteners 50 for releasably engaging a pair of laterally spaced pile fasteners 52 on an inner surface of the waist band of the undergarment. It should be understood that any other type of coupling mechanism may be employed in the present invention including, but not limited to snaps, hooks, magnets, adhesive, or any other means for accomplishing the intended objectives of the present invention.

In use, the incontinence diaper is removably positioned within the undergarment. Further, the buttons of the undergarment are removably inserted within corresponding slits of the incontinence diaper for maintaining fixed relative positioning. This ensures comfort and prevents possible leakage.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An incontinence system comprising, in combination:
    a reusable undergarment constructed from a cloth linen material and including a front portion, a rear portion, and a bottom portion integrally coupled to define a top circular waist opening with a peripheral edge residing in a common plane and a pair of bottom circular leg openings each with a peripheral edge, the undergarment including an elastic waist strap mounted along the peripheral edge of the waist opening and a pair of elastic leg straps mounted along the peripheral edges of the leg openings, the elastic waist strap having an inner surface with a first pair of spaced buttons mounted thereon adjacent to ends of the front portion and a second pair of spaced buttons mounted thereon adjacent to ends of the rear portion such that the first pair of buttons and the second pair of buttons are axially aligned;

a disposable incontinence diaper constructed from an absorbent material and including a front portion, a rear portion, and a bottom portion integrally coupled to define a top circular waist opening with a peripheral edge residing in a common plane and a pair of bottom circular leg openings each with a peripheral edge, the incontinence diaper including an elastic waist strap mounted along the peripheral edge of the waist opening and a pair of elastic leg straps mounted along the peripheral edges of the leg openings, the elastic waist strap having an inner surface with a first pair of spaced horizontal slots formed therein adjacent to ends of the front portion and a second pair of spaced horizontal slots formed therein adjacent to ends of the rear portion such that the first pair of slits and the second pair of slits are aligned;

wherein the incontinence diaper is removably positioned within the undergarment such that the buttons of the undergarment are removably inserted within corresponding slits of the incontinence diaper for maintaining fixed relative positioning.

2. An incontinence system comprising:

a reusable undergarment having a top waist opening with an elastic waist strap mounted along the waist opening, the top waist strap having an inner surface;

a first attachment means mounted directly on the inner surface of the top waist strap of the reusable undergarment;

a disposable incontinence diaper having a top waist opening with an elastic waist strap mounted along the waist opening, the top waist strap having an outer surface;

a second attachment means mounted directly on the outer surface of the top waist strap of the diaper for being removably coupled to the first attachment means;

wherein the first and second attachment means of the undergarment and the incontinence diaper removably mounts the outer surface of the waist strap of the diaper in abutment against the inner surface of the waist strap of the undergarment for maintaining fixed relative positioning therebetween.

3. An incontinence system as set forth in claim 2 wherein the first attachment means includes at least one button and the second attachment means includes at least one slit.

4. An incontinence system as set forth in claim 2 wherein the first attachment means includes a first pile fastener and the second attachment means includes a second pile fastener.

5. An incontinence system as set forth in claim 2 wherein at least one of the first attachment means and the second attachment means includes a button.

6. An incontinence system comprising:

a reusable undergarment constructed from a cloth material and including a front portion, a rear portion, and a bottom portion integrally coupled to define a top waist opening with a peripheral edge residing in a common plane and a pair of bottom leg openings each with a peripheral edge, the undergarment including an elastic waist strap mounted along the peripheral edge of the waist opening and a pair of elastic leg straps mounted along the peripheral edges of the leg openings, the elastic waist strap having an inner surface with a first pair of spaced pile fastener components mounted thereon adjacent to ends of the front portion and a second pair of spaced pile fastener components mounted thereon adjacent to ends of the rear portion;

a disposable incontinence diaper constructed from an absorbent material and including a front portion, a rear portion, and a bottom portion integrally coupled to define a top waist opening with a peripheral edge and a pair of bottom leg openings each with a peripheral edge, the incontinence diaper including an elastic waist strap mounted along the peripheral edge of the waist opening and a pair of elastic leg straps mounted along the peripheral edges of the leg openings, the elastic waist strap having an inner surface with a first pair of spaced pile fastener components mounted thereon adjacent to ends of the front portion and a second pair of spaced pile fastener components mounted thereon adjacent to ends of the rear portion;

wherein the incontinence diaper is removably positioned within the undergarment such that the pile fastener components of the undergarment are removably couplable to the corresponding pile fastener components of the incontinence diaper for maintaining fixed relative positioning of the diaper and the undergarment.

* * * * *